United States Patent
Liu

(10) Patent No.: US 11,494,905 B2
(45) Date of Patent: Nov. 8, 2022

(54) MEDICAL IMAGE RECOGNITION METHOD AND MEDICAL IMAGE RECOGNITION DEVICE

(71) Applicant: Wistron Corp., New Taipei (TW)

(72) Inventor: Ting Yin Liu, New Taipei (TW)

(73) Assignee: WISTRON CORP., New Taipei (TW)

( * ) Notice: Subject to any disclaimer, the term of this patent is extended or adjusted under 35 U.S.C. 154(b) by 134 days.

(21) Appl. No.: 16/918,245

(22) Filed: Jul. 1, 2020

(65) Prior Publication Data

US 2021/0312614 A1     Oct. 7, 2021

(30) Foreign Application Priority Data

Apr. 1, 2020 (TW) .................................. 109111143

(51) Int. Cl.
   *G06N 3/04*             (2006.01)
   *G06T 7/00*             (2017.01)

(52) U.S. Cl.
CPC ......... *G06T 7/0012* (2013.01); *G06N 3/0454* (2013.01); *G06N 3/0472* (2013.01); *G06T 2207/10088* (2013.01); *G06T 2207/20021* (2013.01); *G06T 2207/20076* (2013.01); *G06T 2207/20081* (2013.01); *G06T 2207/20084* (2013.01); *G06T 2207/30004* (2013.01)

(58) Field of Classification Search
None
See application file for complete search history.

(56) References Cited

U.S. PATENT DOCUMENTS

| 2003/0099391 A1* | 5/2003 | Bansal ................. G06T 7/0012 |
| | | 382/173 |
| 2004/0220466 A1* | 11/2004 | Matsumoto .............. G06T 7/60 |
| | | 600/407 |
| 2016/0180528 A1* | 6/2016 | Reynolds ................ A61B 8/08 |
| | | 382/128 |

(Continued)

FOREIGN PATENT DOCUMENTS

| CN | 110599451 A | 12/2019 |
| CN | 209770401 U | 12/2019 |

OTHER PUBLICATIONS

Chinese language office action dated Sep. 4, 2020, issued in application No. TW 109111143.

*Primary Examiner* — Tsung Yin Tsai
(74) *Attorney, Agent, or Firm* — McClure, Qualey & Rodack, LLP

(57) ABSTRACT

A medical image recognition method includes the following steps: establishing an image recognition model, wherein the image recognition model is generated by inputting a plurality of labeled medical image slices in a plurality of initial medical image piles into a neural network; and in response to determining that the accuracy of the image recognition model is not higher than an accuracy threshold; calculating a plurality of image change rates corresponding to each of a plurality of initial medical image slices or the initial medical image piles formed by the initial medical image slices according to the image recognition model; selecting at least one of the initial medical image piles or the initial medical image slices as a training medical image slice according to the image change rates; obtaining the target range of each training medical image slice to re-establish the image recognition model.

20 Claims, 6 Drawing Sheets

(56) References Cited

U.S. PATENT DOCUMENTS

| | | | |
|---|---|---|---|
| 2018/0061058 A1* | 3/2018 | Xu | G06N 3/084 |
| 2019/0130565 A1* | 5/2019 | Lee | G06T 7/30 |
| 2019/0251694 A1* | 8/2019 | Han | G06T 7/11 |
| 2020/0303062 A1* | 9/2020 | Tao | G06V 10/26 |
| 2021/0158936 A1* | 5/2021 | Rao | G06F 3/0488 |

* cited by examiner

MEDICAL IMAGE RECOGNITION METHOD AND MEDICAL IMAGE RECOGNITION DEVICE

CROSS REFERENCE TO RELATED APPLICATIONS

This application claims priority of Taiwan Patent Application No. 109111143, filed on Apr. 1, 2020, the entirety of which is incorporated by reference herein.

BACKGROUND OF THE INVENTION

Field of the Invention

The present disclosure relates to an image recognition method and an image recognition device, and in particular, to a medical image recognition method and a medical recognition device.

Description of the Related Art

Magnetic Resonance Imaging (MRI) examination is an imaging examination tool that does not use radiation, and it can provide clear images of soft tissue. At present, it is widely used in the diagnosis of injury and disease in body parts, such as the brain, knee, elbow, etc. Because of the clear three-dimensional imaging, it is also currently used by obstetricians to monitor the health of mother and fetus. In order to properly monitor these changes, accurate MRI image segmentation of the fetal brain is necessary. Generally, after a series of MRI examinations of pregnant women, the brain of the fetus imaged by MRI will be divided by the radiologist. Because MRI imaging is constructed by multiple two-dimensional images, in addition to the extremely time-consuming establishment of a three-dimensional image of the fetal brain time series, it also requires multiple professional medical personnel.

Therefore, how to assist doctors processing on time-series MRI image segmentation based on the process of sample selection strategy, and how to provide samples with more information for model training to achieve better model performance, with precise automation to generate specific organs or specific parts of the mark in the limited time and medical manpower, is one of the problems needed to be improved in the art.

BRIEF SUMMARY OF THE INVENTION

In accordance with one feature of the present disclosure, the present disclosure provides a medical image recognition method includes following steps: establishing an image recognition model; wherein the image recognition model is generated by inputting a plurality of labeled medical image slices in a plurality of initial medical image piles into a neural network; and in response to determining that the accuracy of the image recognition model is not higher than an accuracy threshold; calculating a plurality of image change rates corresponding to each of a plurality of initial medical image slices or the initial medical image piles formed by the initial medical image slices according to the image recognition model; selecting at least one of the initial medical image piles or the initial medical image slices as a training medical image slice according to the image change rates; obtaining the target range of each of the training medical image slices to re-establish the image recognition model.

In accordance with one feature of the present disclosure, the present disclosure provides a medical image recognition device. The medical image recognition device includes a processor. The processor is configured to establish an image recognition model. The image recognition model is generated by inputting a plurality of labeled medical image slices in a plurality of initial medical image piles into a neural network. The processor is configured to determine whether the accuracy of the image recognition model is higher than an accuracy threshold. When the processor determines that the accuracy of the image recognition model is not higher than the accuracy threshold, the processor calculates a plurality of image change rates corresponding to each initial medical image slice or the initial medical image piles formed by the initial medical image slices according to the image recognition model. The processor selects at least one of the initial medical image piles or the initial medical image slices as a training medical image slice according to the image change rates. The processor obtains the target range of each of the training medical image slices to re-establish the image recognition model.

The medical image recognition method and the medical image recognition device shown in the embodiments of the present invention can accelerate the establishment of the image recognition model. First, the processor randomly selects the initial medical image (i.e., MRI sample) at multiple time points for the MRI data, and the doctor labels the three-dimensional target range (such as the fetal brain). The processor builds an image recognition model based on these samples at multiple time points. The processor uses the volume change rate or area change rate of the target range to select the next training medical image that needs to be trained for the image recognition model, so that the image recognition model can learn more information by limiting the labeled medical image in order to improve the accuracy of the image recognition model prediction. In addition, the medical image recognition method and the medical image recognition device shown in the embodiments of the present invention can establish a high-precision image recognition model for a patient's historical data to reduce the labor cost of manual labeling by the doctor.

BRIEF DESCRIPTION OF THE DRAWINGS

In order to describe the manner in which the above-recited and other advantages and features of the disclosure can be obtained, a more particular description of the principles briefly described above will be rendered by reference to specific examples thereof which are illustrated in the appended drawings. Understanding that these drawings depict only example aspects of the disclosure and are not therefore to be considered to be limiting of its scope, the principles herein are described and explained with additional specificity and detail through the use of the accompanying drawings in which.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The present invention will be described with respect to particular embodiments and with reference to certain drawings, but the invention is not limited thereto and is only limited by the claims. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

Figure 1A:
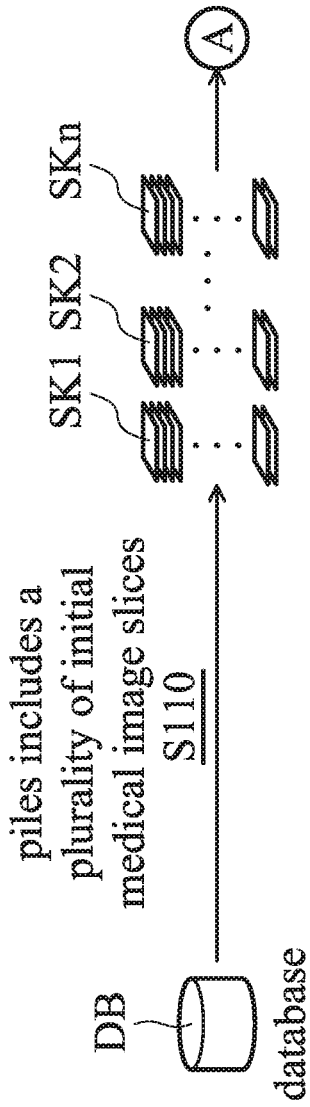
FIGS. 1A-1B are schematic diagrams of an image recognition method in accordance with one embodiment of the present disclosure.
Figure 1B:
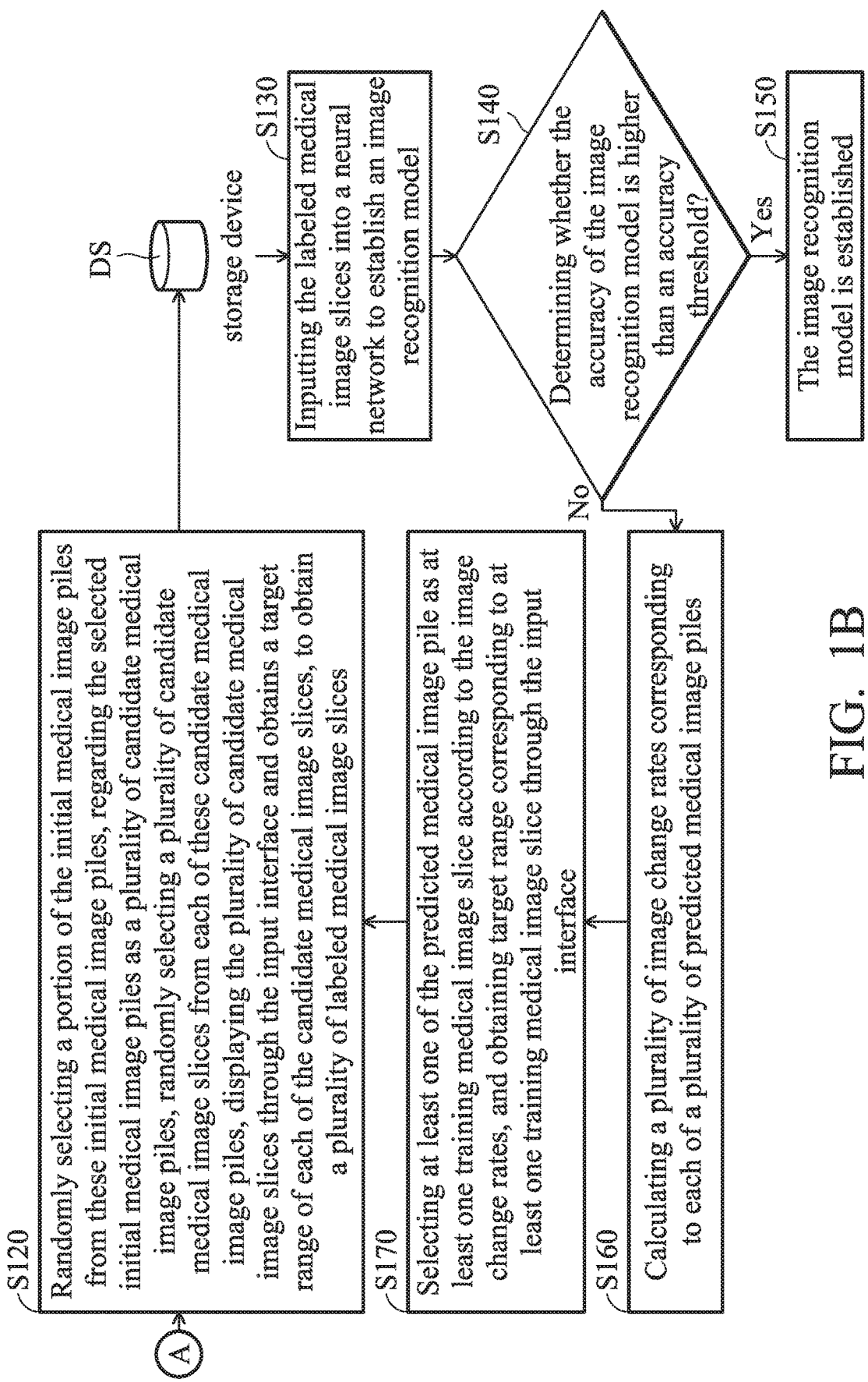
Figure 2:
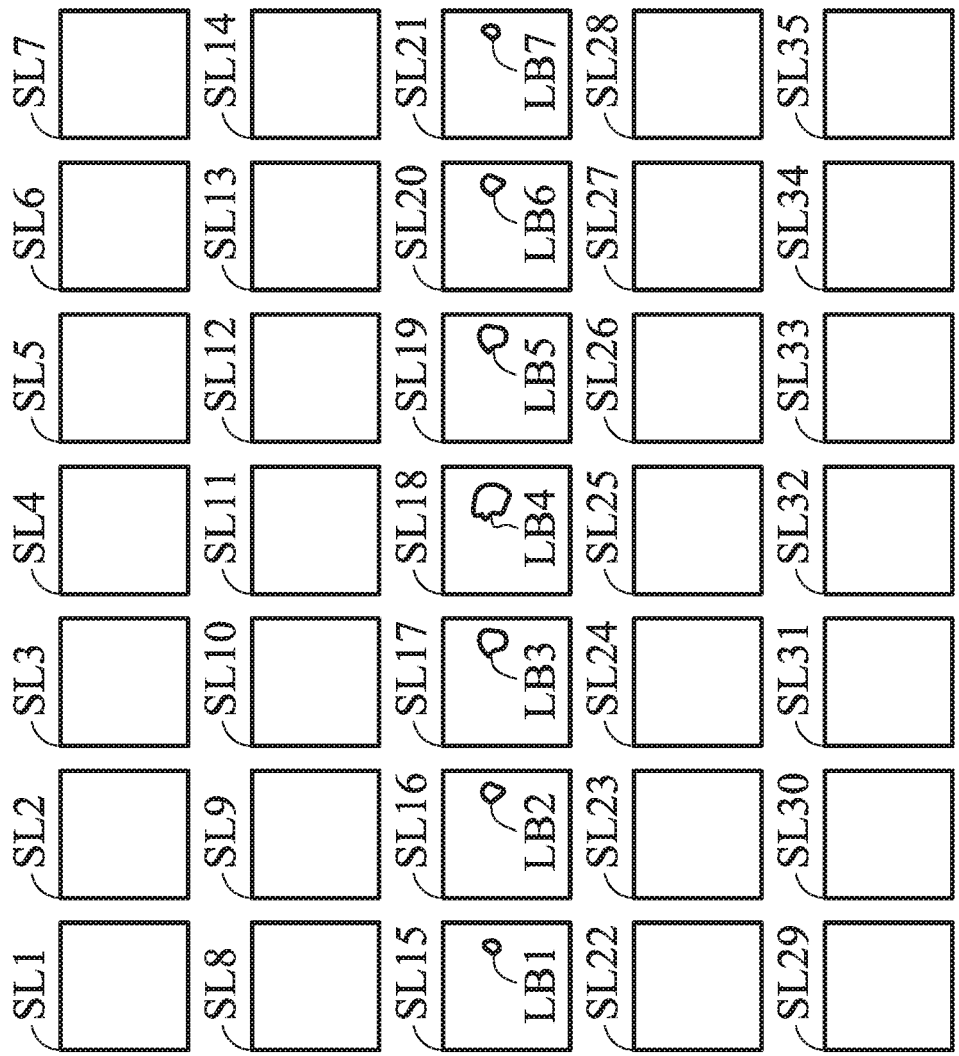
FIG. 2 is a schematic diagram of an initial medical image slice in accordance with one embodiment of the present disclosure.
Figure 3:
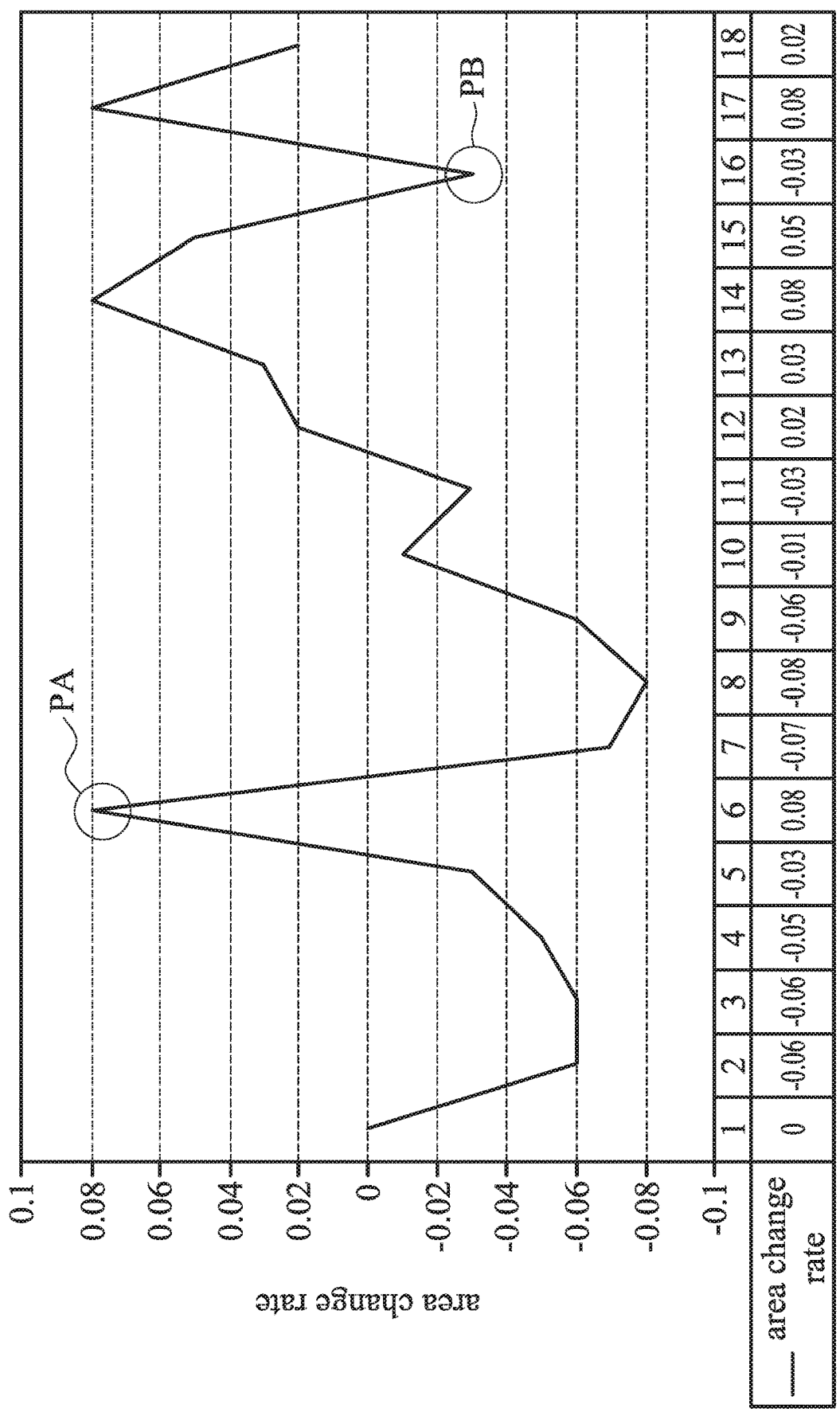
FIG. 3 is a schematic diagram of an image change rates in accordance with one embodiment of the present disclosure.

Please refer to FIGS. 1A-1B and 2-3, FIGS. 1A-1B are schematic diagrams of an image recognition method 100 in accordance with one embodiment of the present disclosure. FIG. 2 is a schematic diagram of an initial medical image slice in accordance with one embodiment of the present disclosure. FIG. 3 is a schematic diagram of an image change rates in accordance with one embodiment of the present disclosure.

In one embodiment, the medical image recognition method 100 may be implemented by a medical image recognition device, and the medical image recognition device includes a processor. In one embodiment, the medical image recognition device further includes a storage device DS (as shown in FIG. 1B). The storage device DS is used to store a database DB. Magnetic Resonance Imaging (MRI) can be stored in the database DB. In one embodiment, the storage device DS can also store X-ray Computed Tomography files. This is a three-dimensional radiographic medical image, so it can also be used to calculate the three-dimensional volume of an organ. The processor is used to execute each step of the medical image recognition method 100.

In one embodiment, the storage device DS can be implemented by a read-only memory, a flash memory, a floppy disk, a hard disk, a compact disk, a flash drive, a magnetic tape, a network accessible database, or a storage medium having the same function by those skilled in the art.

In one embodiment, the processor can be implemented by a microcontroller, a microprocessor, a digital signal processor, an application specific integrated circuit (ASIC) or a logic circuit, but not limited thereto.

In one embodiment, the medical image recognition device may be connected to an apparatus or device for acquiring images.

In step S110, the processor obtains a plurality of initial medical image piles SK1-SKn. Each of these initial medical image piles SK1-SKn includes a plurality of initial medical image slices SL1-SL35.

In one embodiment, the processor reads the initial medical image piles SK1-SKn from the database DB. In other words, initial medical image piles SK1-SKn represent that there are total n piles of initial medical image piles taken at different time points. In another embodiment, the database DB can be stored in a server, and the processor can access the database DB in the server through the communication module.

In one embodiment, each of the initial medical image piles SK1-SKn includes multiple initial medical image slices SL1-SL35.

In one embodiment, initial medical image piles SK1-SKn are multiple MRI images. Each MRI is a three-dimensional volume, usually defined as a frame. Each MRI is composed of multiple two-dimensional images (such as multiple initial medical image slices SL1-SL35). As shown in FIG. 2, the initial medical image pile SK1 contains these 35 initial medical image slices SL1-SL35. In one embodiment, the doctor may mark the target range (for example, the fetal brain) in the initial medical image slices SL1-SL35 by color blocks or frame lines, for example, the range LB1-LB7. In one embodiment, the doctor can mark the target range through the input interface or through the operation interface of the display. The input interface can be, for example, a touch screen, a mouse, a stylus, a keyboard, etc. However, FIG. 2 is only an example, and those of ordinary skill in the art should understand that initial medical image pile SK1 may include more or less than 35 initial medical image slices. For example, initial medical image pile SK1 originally includes 105 initial medical image slices. For convenience of explanation, one initial medical image slice is selected at three intervals, and the 35 initial medical image slices SL1-SL35 are selected as representatives.

In step S120, the processor randomly selects a portion of the initial medical image piles (such as selecting three initial medical image piles SK2, SK5, SK10) from these initial medical image piles SK1-SKn (for example, n is 10 and there are 10 initial medical image piles). The processor regards the selected initial medical image piles SK2, SK5 and SK10 as a plurality of candidate medical image piles. The processor randomly selects a plurality of candidate medical image slices from each of these candidate medical image piles. The processor displays a plurality of candidate medical image slices through the input interface and obtains the target range of each of the candidate medical image slices, to obtain a plurality of labeled medical image slices.

In one embodiment, the display can display multiple candidate medical image slices and obtain the target range through the input interface. For example, the touch screen displays multiple candidate medical image slices, and the doctor selects the target range in multiple candidate medical image slices with the finger or stylus (for example, the doctor selects baby brain range in multiple candidate medical image slices with the finger). In this way, the processor can obtain multiple labeled medical image slices.

In one embodiment, the processor selects at least one of initial medical image piles SK1-SKn or initial medical image slices (such as initial medical image slices SL1-SL35) as a training medical image slice.

The following example takes 10 the initial medical image piles SK1-SK10, and selects initial medical image piles SK2, SK5 and SK10 as an example. However, this is an example, and those with ordinary knowledge in the art should understand that the number of initial medical image piles SK1-SKn is not limited to thereto, and the number of candidate medical image piles is not limited to thereto.

In an embodiment, it is assumed that 10 patients are photographed to obtain initial medical image piles SK1-SK10 corresponding to the 10 patients. The initial medical image pile SK1 is obtained by photographing patient 1, the initial medical image pile SK2 is obtained by photographing patient 2, and so on.

In one embodiment, the initial medical image piles SK1-SK10 each have 15, 23, 18, 20, 17, 15, 15, 25, 30, and 19 initial medical image slices. For example, initial medical image pile SK1 has 15 initial medical image slices, initial medical image pile SK2 has 23 initial medical image slices . . . , and so on. The three-dimensional volumes of initial medical image piles SK1-SK10 are (N*N*15), (N*N*23) . . . , and so on. The symbol N is the length and width of the initial medical image slice (in this example, the length and width are the same).

Next, since the goal is to establish an image recognition model, the accuracy threshold of the image recognition model is set to a certain value, such as 95%. That is, the recognition rate of the image recognition model higher than 95% can be regarded as the completion of the image recognition model. It is also assumed that in addition to the first labeling of candidate imaging slice (which can be manually labeled by the doctor, or based on a labeling signal received by the processor for labeling), each subsequent labeling can only label up to 5 training medical image for saving the labor of labeling manpower and data calculation. The following examples illustrate the detailed technical features of these steps.

In one embodiment, the processor randomly selects three initial medical image piles SK2, SK5 and SK10 from the initial medical image piles SK1-SK10. The processor regards the selected initial medical image piles SK2, SK5 and SK10 as multiple candidate medical image piles. The processor randomly selects 3 candidate medical image slices from each of these candidate medical image piles SK2, SK5 and SK10. The representation method of these candidate medical image slices can be, for example, ($X_5^2$, $X_{11}^2$, $X_{21}^2$, $X_1^5$, $X_9^5$, $X_{15}^5$, $X_6^{10}$, $X_{11}^{10}$, $X_{18}^{10}$). The symbol $X_5^2$ represents the 5th candidate medical image slice in the candidate medical image pile SK2, the symbol $X_{11}^2$ represents the 11th candidate medical image slice in the candidate medical image pile SK2, and so on. In one embodiment, the selected 9 candidate medical image slices are provided to the doctor for labeling, or labeled according to a labeling signal received by the processor, thereby labeling these candidate medical image slices ($X_5^2$, $X_{11}^2$, $X_{21}^2$, $X_1^5$, $X_9^5$, $X_{15}^5$, $X_6^{10}$, $X_{11}^{10}$, $X_{18}^{10}$) each corresponding to a target range (such as fetal brain) to obtain multiple slices of annotated medical images slice ($X_5^2$, $X_{11}^2$, $X_{21}^2$, $X_1^5$, $X_9^5$, $X_{15}^5$, $X_6^{10}$, $X_{11}^{10}$, $X_{18}^{10}$). Since labeling the medical image slice is only used to mark the target range on the candidate medical image slice, the expression of the symbol is unchanged. However, the target range described in this case is not limited to the fetal brain, but can also be knees, elbows, tissues, urine, amniotic fluid, or other body parts.

In one embodiment, the processor divides the labeled medical image slices ($X_5^2$, $X_{11}^2$, $X_{21}^2$, $X_1^5$, $X_9^5$, $X_{15}^5$, $X_6^{10}$, $X_{11}^{10}$, $X_{18}^{10}$) into a training set and a test set and stored in the storage device DS (as shown in FIG. 1B).

In step S130, the processor inputs the labeled medical image slices ($X_5^2$, $X_{11}^2$, $X_{21}^2$, $X_1^5$, $X_9^5$, $X_{15}^5$, $X_6^{10}$, $X_{11}^{10}$, $X_{18}^{10}$) into a neural network to establish an image recognition model.

In one embodiment, the neural network and the image recognition model are stored in the storage device DS in the form of programs, software, and/or firmware, respectively.

In another embodiment, the neural network can be stored in the server. The processor can transmit the labeled medical image slices to the server through the communication module and use the labeled medical image slices as the input data of the neural network.

In one embodiment, the processor inputs the labeled medical image slices belonging to the training set into a neural network to establish the image recognition model.

In one embodiment, the processor inputs labeled medical image slices belonging to the testing set into a neural network to verify the accuracy of the image recognition model.

In one embodiment, the neural network can use Convolutional Neural Networks (CNN), Recurrent Neural Networks (RNN), or other known neural networks that can be used for image processing.

In step S140, the processor determines whether the accuracy of the image recognition model is higher than an accuracy threshold (for example, 95%). If the processor determines that the accuracy of the image recognition model is higher than the accuracy threshold, the step S150 is performed. If the processor determines that the accuracy of the image recognition model is not higher than the accuracy threshold, the step S160 is performed.

In one embodiment, the processor inputs the initial medical image slices corresponding to the labeled medical image slices into the image recognition model, so as to mark a corresponding prediction range in the initial medical image slices by the image recognition model (for example, the processor annotates the predicted fetal brain range in each initial medical image slices through an image recognition model). The processor also calculates an overlapping area of each of the target ranges corresponding to the labeled medical image slices (such as the range of the fetal brain that has been manually marked by the doctor) and the prediction range (that is, the predicted fetal brain range marked by the image recognition model) corresponding to each of the initial medical image slices. The processor divides the overlapping areas by the target ranges corresponding to the labeled medical image slices to obtain a plurality of dice coefficients. When the dice coefficients are all within a range of predetermined values (for example, the difference between the maximum value and the minimum value of the dice coefficients is within 10% of the range of predetermined values), and/or the number of dice coefficients above the accuracy threshold (for example, 95%) exceeds a predetermined ratio (for example, 98% of the dice coefficients are greater than the accuracy threshold), the accuracy of the image recognition model is regarded as being higher than the accuracy threshold. On the contrary, it is regarded that the accuracy of the image recognition model is not higher than the accuracy threshold.

In step S150, in response to determining that the accuracy of the image recognition model is higher than the accuracy threshold (for example, 95%), it means that the image recognition model is established.

In step S160, the processor calculates a plurality of image change rates corresponding to each of a plurality of predicted medical image piles. In one embodiment, the processor inputs all initial medical image piles into the image recognition model to obtain the predicted medical image piles, and calculates the image change rates based on all predicted medical image piles.

In one embodiment, the image change rate refers to, for example, the change relationship of the target range in the medical image slices sorted by time series, for example, the change relationship of the target range in the first medical image slice and the target range in second medical image slice sorted by time. In one embodiment, the image change rate can refer to the area change rate (as shown in FIG. 3), and the algorithm of the area change rate is shown in the subsequent formula (1).

In an embodiment, the image change rate refers to, for example, the change relationship between the target range of the fifth predicted medical image in a first predicted medical image pile and the target range of the fifth predicted medical image in a second predicted medical image. The first predicted medical image pile and the second predicted medical image pile are sorted in time series.

In one embodiment, the image change rate may refer to an area change rate or a volume change rate.

In step S170, the processor selects at least one of the predicted medical image pile as at least one training medical image slice according to the image change rates, and the processor obtains target range corresponding to at least one training medical image slice through the input interface. In one embodiment, the doctor can mark the corresponding target range in at least one training medical image slice through the input interface or through the operation interface of the display, such as a touch screen, mouse, stylus, keyboard, etc.

In one embodiment, the image change rate can refer to the area change rate. The detailed technical features of the area change rate of the image change rate are described below.

In one embodiment, the processor selects the predicted medical image piles corresponding to the initial medical image piles other than the candidate medical image piles SK2, SK5, and SK10 according to the image change rates, and selects at least one of the predicted medical image pile as a training medical image slice.

In one embodiment, when the processor selects at least one of the predicted medical image piles as a training medical image slice according to these image change rates, the processor may select some initial medical image slices other than the aforementioned 9 candidate medical image slices slice ($X_5^2$, $X_{11}^2$, $X_{21}^2$, $X_1^5$, $X_9^5$, $X_{15}^5$, $X_6^{10}$, $X_{11}^{10}$, $X_{18}^{10}$) using for training the image recognition model in the subsequent steps. In other words, in some embodiments, these candidate medical image piles SK2, SK5, and SK10 can also be predicted medical image piles, but the processor will not select labeled medical image slices ($X_5^2$, $X_{11}^2$, $X_{21}^2$, $X_1^5$, $X_9^5$, $X_{15}^5$, $X_6^{10}$, $X_{11}^{10}$, $X_{18}^{10}$) that have been marked as training medical image slices.

In one embodiment, when the processor selects at least one of the predicted medical image piles as at least one training medical image slice according to the image change rates, then the processor selects partial or all of at least one training medical image slice from some of the initial medical image piles SK1, SK3, SK4, SK6, SK7, SK8, and SK9 other than the candidate medical image piles SK2, SK5, and SK10 corresponding to the predicted medical image piles.

By selecting the predicted medical image piles corresponding to these initial medical image piles other than the candidate medical image piles, in the subsequent steps, the sources of training medical image slices used to train the image recognition model are more diverse. This can avoid the situation that the training data of the image recognition model is limited to the candidate image stacks SK2, SK5 and SK10.

In one embodiment, in response to determining that the accuracy of the image recognition model is not higher than the accuracy threshold, the processor inputs all initial medical image piles into the image recognition model to obtain a plurality of predicted medical image piles. The processor calculates a plurality of image change rates corresponding to each of the predicted medical image piles. Taking patient 2 as an example, the initial medical image slices SL1-SL23 are in the initial medical image pile SK2. After inputting the initial medical image slices SL1-SL23 into the image recognition model, the corresponding predicted medical image pile SK2 is obtained, and the algorithm of the area change rate is as the formula (1):

$$\text{image change rate} = \frac{\text{target area of } x_{i-1}^2 - \text{target area of } x_i^2}{\text{target area of } x_{i-1}^2}, \quad (1)$$

$$i \in [1, 23]$$

That is, the processor subtracts the target area of target range of the i-th predicted medical image slice in the predicted medical image pile SK2 from the target area of target range of the i-lth predicted medical image slice in the predicted medical image pile SK2 (for example, the area of the organ) to obtain an area difference. The processor divides the area difference by the target area of target range of the i-lth predicted medical image slice to obtain the image change rate corresponding to the i-th predicted medical image slice. In this example, a total of 23 values will be calculated because there are 23 slices in the predicted medical image pile SK2.

In addition, the area change rates of the other predicted medical image piles (for example, the processor selects initial medical image piles SK1, SK3, SK4, SK6, SK7, SK8 and SK9 as predicted medical image piles) can also be calculated by the formula (1). In the following paragraphs will use the data of patient 3 and FIG. 3 to illustrate again.

Since the predicted medical image pile SK2 contains labeled candidate medical image slices ($X_5^2$, $X_{11}^2$, $X_{21}^2$), in this embodiment, the maximum absolute value of the area change calculated by before and after the candidate medical image slices ($X_5^2$, $X_{11}^2$, $X_{21}^2$) is used as the change rate threshold. For example, the change rates of the area before and after patient 2's candidate medical image slices ($X_5^2$, $X_{11}^2$, $X_{21}^2$) are (3%, 5%, 4%, 4.5%, −1.5%, −6%). The processor takes the plus or minus 6% as the change rate threshold of patient 2. If a change rate of a predicted medical image slice exceeds this change rate threshold and is a predicted medical image slice other than the predicted medical image slices ($X_5^2$, $X_{11}^2$, $X_{21}^2$) in the predicted medical image pile SK2, the predicted medical image slice can be passed to the doctor as a training medical image slice labeling by manual in the next time.

In one embodiment, when the area of the target range of each of the predicted medical image piles SK1, SK3, SK4, SK6, SK7, SK8 and SK9 increases gradually with time, the predicted medical image piles with positive image change rates is selected by the processor as the training medical image slice. It can be seen from formula (1) that when the area of the target range of each of the predicted medical image piles SK1, SK3, SK4, SK6, SK7, SK8, and SK9 is gradually increased, the image change rate should be negative. Thus, the predicted medical image piles with positive image change rates may have abnormalities. Therefore, the processor selects the predicted medical image piles with positive image change rates as the training medical image slices. Conversely, when the area of the target range of each of the predicted medical image piles SK1, SK3, SK4, SK6, SK7, SK8, and SK9 is gradually decreased, the image change rate should be positive. Thus, the predicted medical image piles with negative image change rates may have abnormalities. Therefore, the processor selects the predicted medical image piles with negative image change rates as the training medical image slices. In one embodiment, when the area of the target range of each of the predicted medical image piles SK1, SK3, SK4, SK6, SK7, SK8, and SK9 is gradually decreased, the processor selects the predicted medical image piles with negative image change rates as the training medical image slices.

In one embodiment, the processor selects each predicted medical image pile SK1, SK3, SK4, SK6, SK7, SK8, and SK9 with predicted medical image piles whose image change rates is greater than the change rate threshold as training medical image slices.

In one embodiment, even when candidate medical image piles SK2, SK5, and SK10 include: the candidate medical image slices whose the image change rates are positive when the areas of the target ranges are gradually increasing with time sequence, the candidate medical image slices whose the image change rates are negative when the areas of the target ranges are gradually decreasing with time sequence, or the candidate medical image slice whose image change rate is greater than the change rate threshold, when it is predicted that the number of training medical image slices selected from the predicted medical image piles SK1, SK3, SK4, SK6, SK7, SK8, and SK9 is already greater than the number of slices that can be marked by the doctor per round (for example, the doctor can only mark 5 slices per round), the processor will not select the candidate medical image slices in candidate medical image piles SK2, SK5 and SK10 as the training medical image slices.

For example, the predicted medical image piles SK1, SK3, SK4, SK6, SK7, SK8, and SK9 corresponding to patients 1, 3, 4, 6, 7, 8, and 9 do not contain labeled medical image slices. The default change rate threshold is 10%. The area of the target range with medical images will gradually increase and then decrease (refer to FIG. 2). The processor finds a predicted medical image slice with a positive image change rate when the area of the target range is increasing in time sequence, and a predicted medical image slice with negative image change rate when the area of the target range is decreasing in time sequence, or a predicted medical image slice with an image change rate greater than the change rate threshold with 10%. In this way, according to the increasing and decreasing trend of the area of the target range, the processor finds out the predicted medical image slices/piles that do not meet the trend, or find the predicted medical image slices/piles whose image change rate is too high, and then apply these specific predicted medical image slices/piles as training medical image slices, to achieve the effect of increasing sample diversity.

In one embodiment, the image change rate may refer to the area change rate of an organ. Assume that the area change rate of the predicted medical image pile SK3 corresponding to patient 3 is shown in FIG. 3. The first column of the X-axis of FIG. 3 is the number of slices (i.e., predicted medical image slices sorted by time series). Assumes 18 predicted medical image slices in the predicted medical image piles SK3 corresponding to patient 3. The second column of the X-axis is the area change rates of each predicted medical image slice calculated by the above formula (1).

The predicted medical image pile SK3 does not contain labeled medical image slice. The processor finds a predicted medical image slice with a positive image change rate when the area of the target range is increasing in time sequence, a predicted medical image with negative image change rate when the area of the target range is decreasing in time sequence, or a predicted medical image slice with an image change rate greater than the change rate threshold with 10%.

It can be seen from FIG. 3 that the image change rate of each adjacent two predicted medical image slice does not exceed 10%. On the other hand, according to the characteristics of the predicted medical image slices, the areas of the organ will gradually increase and then decrease, the processor determines that the area of the target range of the predicted medical image slices from 1st to 11th are in an increasing trend, and the change rates should be negative. At this time, the processor can find that the change rate of the 6th predicted medical image slice is positive (marked with the symbol PA), and then the processor selects the 6th predicted medical image slice as a training medical image slice. In addition, the processor determines that the area of the target range of the predicted medical image slices from 12th to 18th are in a decreasing trend, and the change rates should be positive. At this time, the processor can find that the change rate of the 16th predicted medical image slice is negative (marked with the symbol PB), and then the processor selects the 16th predicted medical image slice as a training medical image slice.

Therefore, according to the line graph of the image change rate in FIG. 3, the processor will select the 6th and 16th predicted medical image slices in the predicted medical image pile SK3 as training medical image slices.

In one embodiment, it is assumed that the area change rates of the predicted medical image piles SK3, SK6, SK8, SK9, and SK10 corresponding to the patients 3, 6, 8, 9, and 10 have the predicted medical slice(s) including the following conditions: a predicted medical image slice with a positive image change rate when the area of the target range is increasing in time sequence, a predicted medical image with negative image change rate when the area of the target range is decreasing in time sequence, or a predicted medical image slice with an image change rate greater than the change rate threshold with 10%. The predicted medical image slices that meet one of these conditions are ($X_6^3$, $X_{16}^3$, $X_{10}^6$, $X_7^8$, $X_{23}^8$, $X_{15}^9$, $X_{19}^9$, $X_{25}^9$, $X_2^{10}$, $X_9^{10}$). The doctor can only manually mark 5 MRI images per round. Therefore, among the 5 patients, in order to increase the diversity of the samples, the 5 predicted medical image slices of the predicted medical image piles SK3, SK6, SK8, and SK9 corresponding to the patients 3, 6, 8, and 9 that have not been labeled will be selected firstly. In the case where it is expected that each patient has at least one labeled medical image slice, it is assumed that the predicted medical image slices ($X_{16}^3$, $X_{10}^6$, $X_7^8$, $X_{15}^9$, $X_{25}^9$) is selected as training medical image slices. When the doctor manually marks these training medical image slices ($X_{16}^3$, $X_{10}^6$, $X_7^8$, $X_{15}^9$, $X_{25}^9$) through the input interface, the processor regards these training medical image slices ($X_{16}^3$, $X_{10}^6$, $X_7^8$, $X_{15}^9$, $X_{25}^9$) as labeled medical image slices.

Next, the processor adds the aforementioned 9 which are labeled medical image slices including ($X_5^2$, $X_{11}^2$, $X_{21}^2$, $X_1^5$, $X_9^5$, $X_{15}^5$, $X_6^{10}$, $X_{11}^{10}$, $X_{18}^{10}$) and the labeled medical image slices ($X_{16}^3$, $X_{10}^6$, $X_7^8$, $X_{15}^9$, $X_{25}^9$) marked by the doctors in this round. Therefore, the processor inputs total of 14 MRI slices into the image recognition model for training the image recognition model again (second round of training).

If the image recognition model has not yet reached the standard, then the processor inputs all the initial medical image piles into the image recognition model again. The processor selects slices other than ($X_5^2$, $X_{11}^2$, $X_{21}^2$, $X_1^5$, $X_9^5$, $X_{15}^5$, $X_6^{10}$, $X_{11}^{10}$, $X_{18}^{10}$) and ($X_{16}^3$, $X_{10}^6$, $X_7^8$, $X_{15}^9$, $X_{25}^9$) as training medical image slices according to the image change rate. For example, after the second round of image recognition model is generated, the above step S140 is repeated in sequence. If the determination in step S140 is NO, the steps S160-S170, S120-S130 are performed. Until the determination in S140 is YES, the step S150 is performed to complete the establishment of the image recognition model.

In one embodiment, the image change rate can refer to the volume change rate. The detailed technical characteristics of the image change rate referring to the volume change rate are described below.

Figure 4:
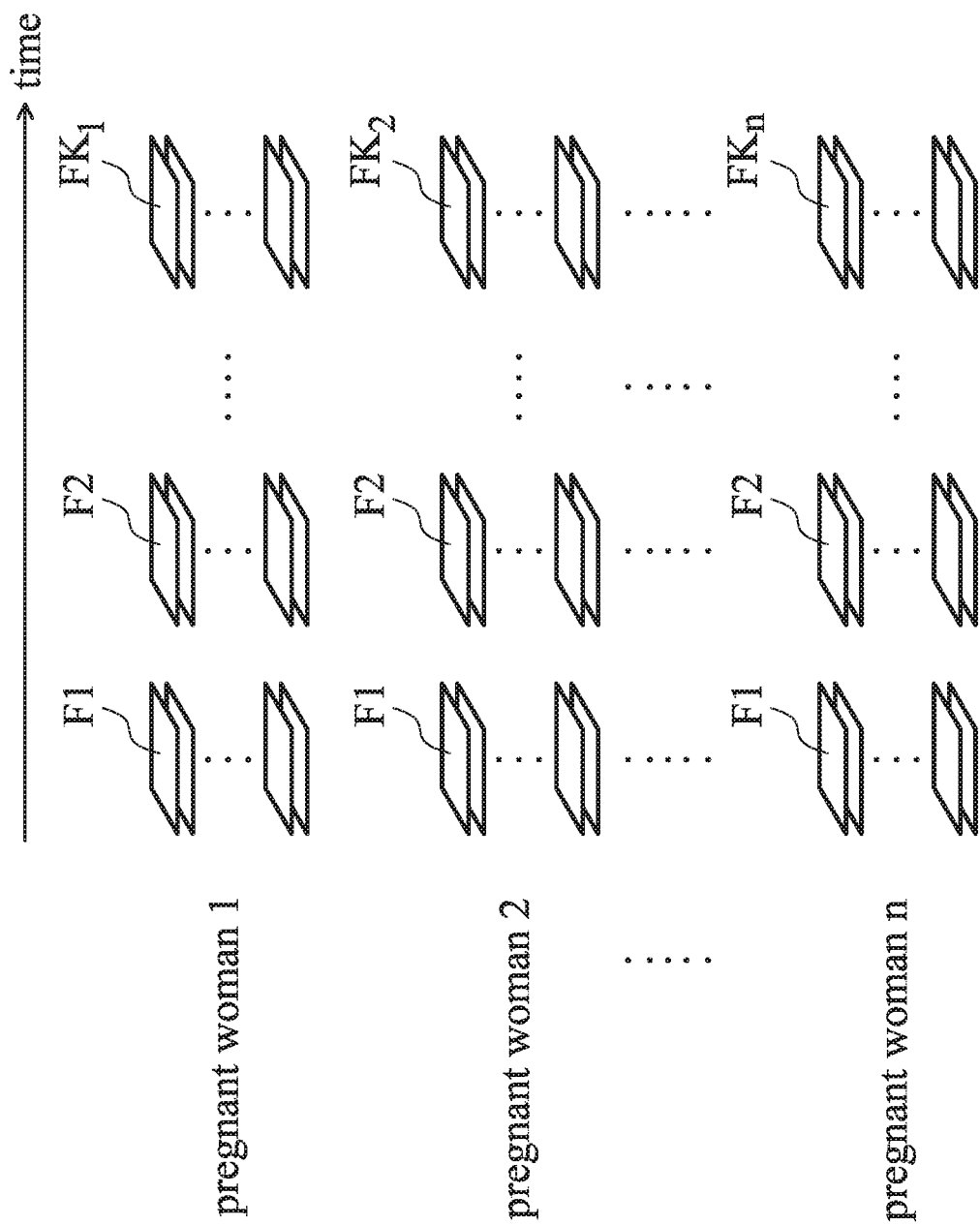
FIG. 4 is a schematic diagram of an initial medical image pile in accordance with one embodiment of the present disclosure.
Figure 5:
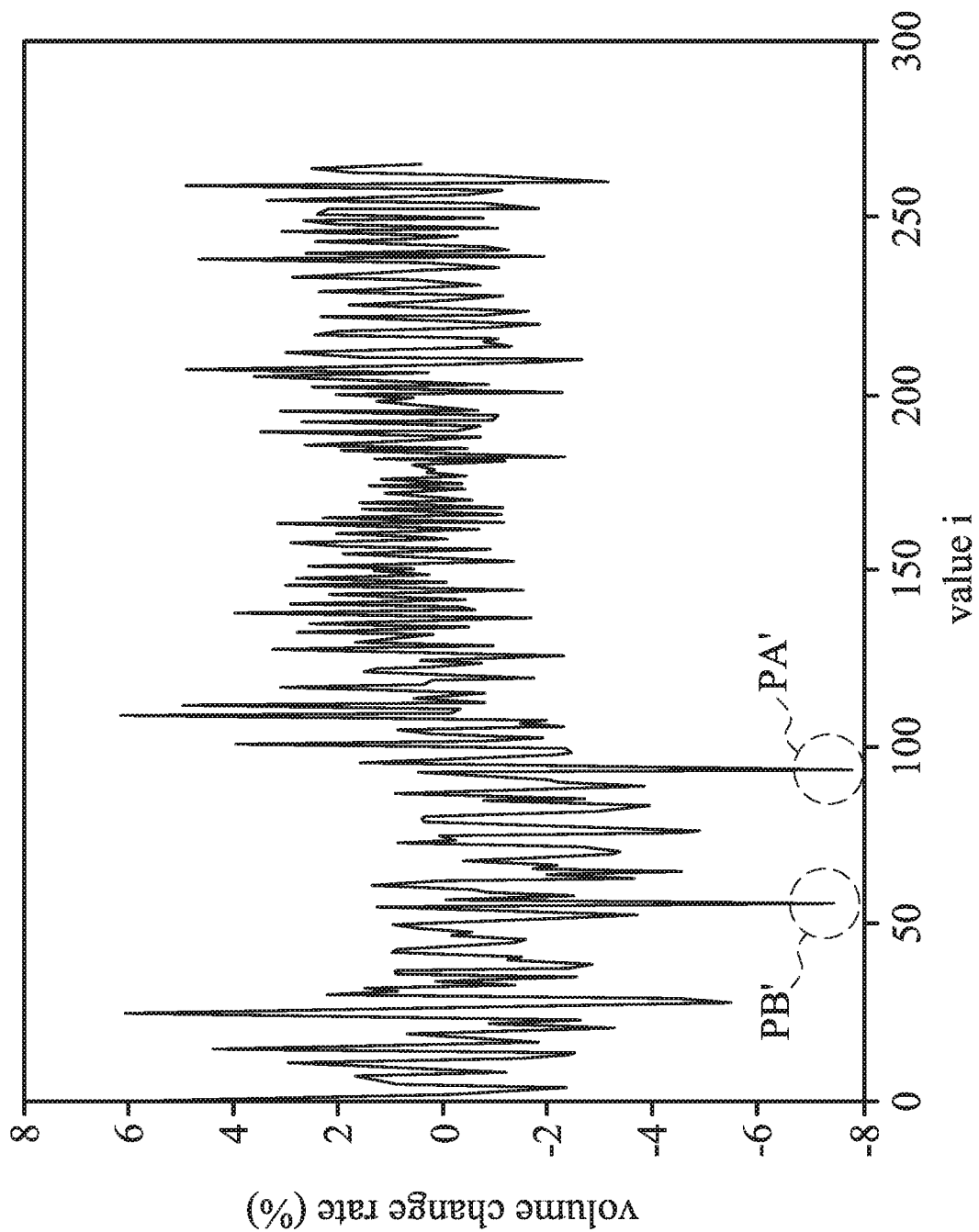
FIG. 5 is a schematic diagram of a volume change rate in accordance with one embodiment of the present disclosure.

Please refer to FIGS. 4-5, FIG. 4 is a schematic diagram of an initial medical image pile in accordance with one embodiment of the present disclosure. FIG. 5 is a schematic diagram of a volume change rate in accordance with one embodiment of the present disclosure.

In an embodiment, as shown in FIG. 4, assuming that n pregnant women perform $K_1$, $K_2$, and Kn MRI examinations ($K_1$, $K_2$, and Kn may be the same or different integer values), respectively, the processor will generate multiple initial medical image piles as shown in FIG. 4. Each initial medical image pile is an MRI image, also known as a frame. The initial medical image pile of the first pile corresponding to pregnant woman 1 is represented by the symbol F1 (representing the initial medical image pile taken during the first MRI examination of pregnant woman 1), and the initial medical image pile of the second pile is represented by the symbol F2 (representing the initial medical image pile taken during the second MRI examination of pregnant woman 1) . . . the initial medical image pile of the $FK_1$th pile is represented by the symbol $FK_1$ (representing the initial medical image pile taken during the $K_1$th MRI examination of pregnant woman 1). The initial medical image pile of the first pile corresponding to the pregnant woman 2 is represented by the symbol F1, the initial medical image pile of the second pile is represented by the symbol F2 . . . the initial medical image pile of the $FK_2$ pile is represented by the symbol $FK_2$. The initial medical image pile of the first pile corresponding to the pregnant woman n is denoted by symbol F1, the initial medical image pile of the second pile is denoted by symbol F2 . . . the initial medical image pile of the FKn pile is denoted by symbol FKn. Each initial medical image pile is obtained by performing an MRI examination, and each initial medical image pile is a three-dimensional image.

In one embodiment, the processor can obtain the organ volume by accumulating the marked organ area in each initial medical image.

When the image change rate refers to the volume change rate, the medical image recognition method 200 can still be used. The steps S110-S170 will not be repeated. The following describes the differences in the technical features of the details when the image change rate refers to the volume change rate and when the image change rate refers to the area change rate.

In one embodiment, in step S140 that the processor determines whether the accuracy of the image recognition model is higher than the accuracy threshold, the processor selects the labeled medical image slices belonging to the candidate medical image piles. The processor inputs the initial medical image slices corresponding to the labeled medical image slices into the image recognition model to mark a corresponding prediction range in the initial medical image slices. The processor calculates each overlapping volume of each target range with the target range of each labeled medical image slice and the prediction range of each initial medical image slice. The processor divides each overlapping volume by the target range of each corresponding labeled medical image slice to obtain a plurality of dice coefficients. When the dice coefficients are all in a range of predetermined values, or the number of dice coefficients above the accuracy threshold exceeds a predetermined ratio, the accuracy of the image recognition model is considered to be higher than the accuracy threshold.

In one embodiment, the processor accumulates the prediction range (area) in multiple initial medical image slices, and the accumulated value is regarded as a volume. For example, the processor accumulates the predicted range (area) in each initial medical image slice of the second initial medical image pile, and the value obtained after the accumulation is regarded as a volume.

In one embodiment, the processor subtracts the first target range of the first predicted medical image slice in the predicted medical image piles from the second target range of the second predicted medical image slice in the predicted medical image piles, thereby obtaining the difference in volume. Moreover, the processor divides the area difference by the first target range of the first predicted medical image to obtain one of the volume change rates. The target range may refer to the target volume or target area.

In one embodiment, the processor selects all of the initial medical image piles (the first to the 255th piles of initial medical image piles corresponding to pregnant woman 1). The processor inputs these initial medical image piles into the image recognition model to obtain the corresponding predicted medical image piles. The processor calculates the volume change rate corresponding to each of the predicted medical image piles (e.g., as shown in FIG. 5, the corresponding volume change rates of the first to the 255th piles of the predicted medical image piles).

In one embodiment, the predicted medical image piles shown in FIG. 5 are time-sequential, and the larger the value of the X axis represents the later time point to obtain the initial medical image pile. For example, a value i of 200 represents the 200th pile of predicted medical image pile, and the value i of 150 represents the 150th pile of predicted medical image pile. According to the time-sequential, the shooting time point of the predicted medical image pile with the value i of 200 is later than that of the predicted medical image stack with the value i of 150.

If there exists labeled images, the processor can calculate the ground truth volume of labeled images, and regard the volume as the first target range. The processor calculates the volume change rate of the predicted target range (for example, the second target range) and the first target range at each time point. When the volume change rate is large, the processor can know that the image at a certain time (for example, the initial image pile corresponding to the predicted medical image pile with an i value of 52) should have some features that cannot be captured by the current image recognition model. Therefore, the processor labels such images and puts them into the training set for retraining. If the initial medical image piles of a pregnant woman do not have any manually labeled samples at all, the processor can select the volume of any target range corresponding to a time point as the baseline volume. The processor calculates the volume change rate from the volume at other time points and the volume at the selected time point. When the volume change rate (shown as PA') at a certain point in time is significantly different from the reference volume, it means that the image recognition model has a different change in the prediction result of the predicted medical image pile at this time from other time points. This is worth observing and labeling.

In one embodiment, the processor selects each of the predicted medical image piles with volume change rate greater than the change rate threshold as a training medical image pile. Moreover, the processor obtains the target ranges for each of the training medical image piles. In one embodiment, the doctor can label the target range of at least one training medical image slice through the input interface or through the operation interface of the display, such as a touch screen, mouse, stylus, or keyboard.

In one embodiment, the processor selects the predicted medical image pile corresponding to the largest of the volume change rates as a training medical image pile. Moreover, the processor obtains the corresponding target ranges of the training medical image piles through the input interface or through the operation interface of the display. As shown in FIG. 5, assuming that the doctor can label two piles of predicted medical image piles, the processor selects the corresponding predicted medical image piles of the largest volume change rate (the 98th pile, marked with the symbol PA') and the next largest (the 52nd pile, marked with the symbol PB') as the training medical image piles.

For example, suppose there are 10 pregnant women, each of whom has (15, 23, 18, 20, 17, 15, 15, 25, 30, 19) initial medical image piles. Each value in parentheses represents the number of initial medical image piles corresponding to the 10 pregnant women (i.e., the number of MRI images). For example, pregnant woman 1 has 15 piles of MRI images, and pregnant woman 2 has 23 piles of MRI images. The MRI images are expressed in a sequence according to the time of shooting, and each is sorted by time as $(X_1^1, \ldots, X_{15}^1)$, $(X_1^2, \ldots, X_{23}^2)$, $(X_1^3, \ldots, X_{18}^3)$, $(X_1^4, \ldots, X_{20}^4)$, $(X_1^5, \ldots, X_{17}^5)$, $(X_1^6, \ldots, X_{15}^6)$, $(X_1^7, \ldots, X_{15}^7)$.

It is assumed that the goal is to build an image recognition model, the accuracy must be above 95%, and the change rate threshold is set to 10%, in addition to the first manual labeling, the doctor can only manually label 2 MRI images per round.

Then, the processor randomly selects MRI images of 5 pregnant women from 10 pregnant women. The processor selects $(X_{12}^2, X_8^3, X_{13}^5, X_{17}^8, X_3^{10})$, and these 5 MRI images are manually labeled by the doctor. The symbol $X_{12}^2$ represents the 12th pile of MRI images of the second pregnant woman. The symbol $X_8^3$ represents the 8th pile of MRI images of the third pregnant woman . . . and so on.

The processor performs model training on the marked MRI image to obtain an image recognition model (this may be called an initial image recognition model). If the performance of the image recognition model has not yet reached the threshold of accuracy, the image recognition model is used for predicting $(X_{12}^2, X_8^3, X_{13}^5, X_{17}^8, X_3^{10})$ and other MRI images. Since pregnant women 2, 3, 5, 8, and 10 have manually labeled medical images $(X_{12}^2, X_8^3, X_{13}^5, X_{17}^8, X_3^{10})$, the processor can calculate the volume change rate of the target volume predicted according to other MRI images and the manually labeled target volume. Take pregnant woman 2 as an example, that is, the processor calculates $$\frac{targe \text{ volume of } x_i^2 - targe \text{ volume of } x_{12}^2}{targe \text{ volume of } x_{12}^2},$$

$i \in [1, 23] \text{ \& } i \neq 12$.

The pregnant women 1, 4, 6, 7, 9 do not have manually labeled medical images. Therefore, the processor temporarily uses the fetal brain volume of the first frame of MRI images $(X_1^1, X_1^4, X_1^6, X_1^7, X_1^9)$ as a reference point to calculate the fetal brain volume and the volume change rate of fetal brain volume in the first frame of the MRI image.

Assuming that pregnant women 2, 4, 6, 8, 9, and 10 all have MRI images corresponding to volume change rates greater than the change rate threshold with 10%, their volume change rates are ranked according to the largest to the smallest as $(X_{20}^2 > X_2^2 > X_6^2)$, $(X_{11}^4 > X_{17}^4)$, $(X_7^6)$, $(X_3^8 > X_9^8 > X_{24}^8)$, $(X_{20}^9 > X_4^9 > X_{13}^9)$, $(X_2^{10} > X_{18}^{10})$. Because the doctor can only manually label 2 MRI images per round, among the 6 pregnant women, in order to increase the sample diversity, the processor firstly selects any two pregnant women from pregnant women 4, 6, and 9. Assuming that pregnant women 4 and 9 are selected, the processor selects $X_{11}^4$ and $X_{20}^9$ for the doctor to manually label.

The processor trains the image recognition model again with 7 MRI images of $(X_{12}^2, X_8^3, X_{13}^5, X_{17}^8, X_3^{10})$ and $(X_{11}^4, X_{20}^9)$ to obtain the second round of image recognition model. If the performance capability of this second round of image recognition model has not reached the accuracy threshold, the image recognition model is used for predicting $(X_{12}^2, X_8^3, X_{13}^5, X_{17}^8, X_3^{10})$, $(X_{11}^4, X_{20}^9)$ and other MRI images.

Currently, the pregnant women 2, 3, 4, 5, 8, 9 and 10 have manually labeled images. Therefore, the processor can calculate the volume change rate of other MRI images and the manually labeled fetal brain volume. The pregnant women 1, 6 and 7 don't have manually labeled images. Therefore, the processor still temporarily uses the target volume of the first frame of MRI images $(X_1^1, X_1^6, X_1^7)$ as a reference point to calculate the volume change rate of the target volume of other MRI images and the target volume of the first frame of MRI image. Then, the processor again selects the MRI images of the two pregnant women whose volume change rate is greater than the change rate threshold with 10%, to process manually labeling, and repeats the above steps until the accuracy of the image recognition model is greater than or equal to the accuracy threshold.

The medical image recognition method and the medical image recognition device shown in the embodiments of the present invention can accelerate the establishment of the image recognition model. First, the processor randomly selects the initial medical image (i.e., MRI sample) at multiple time points for the MRI data, and the doctor labels the three-dimensional target range (such as the fetal brain). The processor builds an image recognition model based on these samples at multiple time points. The processor uses the volume change rate or area change rate of the target range to select the next training medical image that needs to be trained for the image recognition model, so that the image recognition model can learn more information by limiting the labeled medical image in order to improve the accuracy of the image recognition model prediction. In addition, the medical image recognition method and the medical image recognition device shown in the embodiments of the present invention can establish a high-precision image recognition model for a patient's historical data to reduce the labor cost of manual labeling by the doctor.

Although the invention has been illustrated and described with respect to one or more implementations, equivalent alterations and modifications will occur or be known to others skilled in the art upon the reading and understanding of this specification and the annexed drawings. In addition, while a particular feature of the invention may have been

What is claimed is:

1. A medical image recognition method, comprising:
   establishing an image recognition model; wherein the image recognition model is generated by inputting a plurality of labeled medical image slices in a plurality of initial medical image piles into a neural network; and
   in response to determining that an accuracy of the image recognition model is not higher than an accuracy threshold, calculating a plurality of image change rates corresponding to each of a plurality of initial medical image slices or the initial medical image piles formed by the initial medical image slices according to the image recognition model; selecting at least one of the initial medical image piles or the initial medical image slices as at least one training medical image slice according to the image change rates; and obtaining a target range corresponding to each of the at least one training medical image slice to re-establish the image recognition model;
   wherein in the step of calculating the image change rates corresponding to each of the initial medical image slices or the initial medical image piles formed by the initial medical image slices according to the image recognition model, the medical image recognition method further comprising:
   wherein the image change rates refer to a plurality of area change rates or a plurality of volume change rates;
   wherein the at least one training medical image slice excludes the labeled medical image slices;
   wherein the target range corresponding to the training medical image is obtained through an operation interface or input interface of a display.

2. The medical image recognition method of claim 1, wherein the establishment of the image recognition model is completed when it is determined that the accuracy of the image recognition model is higher than the accuracy threshold.

3. The medical image recognition method of claim 1, further comprising:
   inputting the initial medical image slices corresponding to the labeled medical image slices into the image recognition model to mark a prediction range corresponding to each of the initial medical image slices;
   calculating an overlapping area of each of the target ranges corresponding to the labeled medical image slices and the prediction range corresponding to each of the initial medical image slices; and
   dividing the overlapping areas by the target ranges corresponding to the labeled medical image slices to obtain a plurality of dice coefficients;
   wherein, in response to the dice coefficients are all within a range of predetermined values, or the number of the dice coefficients above the accuracy threshold exceeds a predetermined ratio, the accuracy of the image recognition model is regarded as being higher than the accuracy threshold.

4. The medical image recognition method of claim 1, wherein in the step of calculating the image change rates corresponding to each of the initial medical image slices or the initial medical image piles formed by the initial medical image slices according to the image recognition model, the medical image recognition method further comprises:
   wherein a plurality of predicted medical image piles is obtain by the image recognition model based on the initial medical image piles formed by the initial medical image slices.

5. The medical image recognition method of claim 4, wherein in the step of calculating the image change rates corresponding to each of the initial medical image slices or the initial medical image piles formed by the initial medical image slices according to the image recognition model, the medical image recognition method further comprises:
   subtracting a first target range corresponding to a first predicted medical image slice in the predicted medical image piles from a second target range corresponding to a second predicted medical image slice in the predicted medical image piles, so as to obtain an area difference; and
   dividing the area difference by the first target range corresponding to the first predicted medical image slice to obtain one of the image change rates.

6. The medical image recognition method of claim 4, wherein the step of selecting at least one of the initial medical image piles or the initial medical image slices as at least one training medical image slice according to the image change rates further comprises:
   when the area of the target range corresponding to each of a plurality of predicted medical image slices in each predicted medical image pile increases gradually with time, the predicted medical image slices with positive image change rate is selected as the at least one training medical image slice; and,
   when the area of the target range corresponding to each of the plurality of predicted medical image slices in each predicted medical image pile decreases gradually with time, the predicted medical image slices with negative image change rate is selected as the at least one training medical image slice.

7. The medical image recognition method of claim 4, wherein the step of selecting at least one of the initial medical image piles or the initial medical image slices as at least one training medical image slice according to the image change rates further comprises:
   selecting the initial medical image piles or the initial medical image slices corresponding to the predicted medical image pile or a plurality of predicted medical image slices with the image change rate greater than a change rate threshold as the at least one training medical image slice.

8. The medical image recognition method of claim 4, wherein in the step of calculating a plurality of image change rates corresponding to each of a plurality of initial medical image slices or the initial medical image piles formed by the initial medical image slices according to the image recognition model, the medical image recognition method further comprises:
   subtracting a first target volume corresponding to a first predicted medical image pile in the predicted medical image piles from a second target volume corresponding to a second predicted medical image pile in the predicted medical image piles, so as to obtain a volume difference; and
   dividing the volume difference by the second target volume to obtain one of the volume change rates.

9. The medical image recognition method of claim 4, further comprising:
selecting the predicted medical image pile in which the corresponding volume change rate is greater than the change rate threshold as at least one training medical image pile; and
obtaining the target range corresponding to each of the at least one training medical image pile.

10. The medical image recognition method of claim 9, further comprising:
selecting the predicted medical image pile corresponding to the largest of these volume change rates as a training medical image pile; and
obtaining the target range corresponding to each of the at least one training medical image pile.

11. The medical image recognition method of claim 1, further comprising:
inputting the initial medical image slices corresponding to the labeled medical image slices into the image recognition model to mark a prediction range corresponding to each of the initial medical image slices;
calculating an overlapping volume of each of the target ranges corresponding to the labeled medical image slices and the prediction range corresponding to each of the initial medical image slices; and
dividing the overlapping volume by the target ranges corresponding to the labeled medical image slices to obtain a plurality of dice coefficients;
wherein in response to the dice coefficients are all within a range of predetermined values, or the number of the dice coefficients above the accuracy threshold exceeds a predetermined ratio, the accuracy of the image recognition model is regarded as being higher than the accuracy threshold.

12. A medical image recognition device, comprising:
a processor, configured to establish an image recognition model; wherein the image recognition model is generated by inputting a plurality of labeled medical image slices in a plurality of initial medical image piles into a neural network, and determining whether the accuracy of the image recognition model is higher than an accuracy threshold;
wherein, in response to determining that the accuracy of the image recognition model is not higher than an accuracy threshold, the processor calculates a plurality of image change rates corresponding to each of a plurality of initial medical image slices or the initial medical image piles formed by the initial medical image slices according to the image recognition model; the processor selects at least one of the initial medical image piles or the initial medical image slices as a training medical image slice according to the image change rates; and the processor obtains a target range corresponding to each of the at least one training medical image slice to re-establish the image recognition model;
wherein the image change rates refer to a plurality of area change rates or a plurality of volume change rates;
wherein the at least one training medical image slice excludes the labeled medical image slices;
wherein the target range corresponding to the training medical image is obtained through an operation interface or input interface of a display.

13. The medical image recognition device of claim 12, wherein the establishment of the image recognition model is completed when the processor determines that the accuracy of the image recognition model is higher than the accuracy threshold.

14. The medical image recognition device of claim 12, wherein the processor is further configured to input the initial medical image slices corresponding to the labeled medical image slices into the image recognition model to mark a prediction range corresponding to each of the initial medical image slices; calculate an overlapping area of each of the target ranges corresponding to the labeled medical image slices and the prediction range corresponding to each of the initial medical image slices; and divide the overlapping areas by the target ranges corresponding to the labeled medical image slices to obtain a plurality of dice coefficients; and in response to the dice coefficients are all within a range of predetermined values, or the number of dice coefficients above the accuracy threshold exceeds a predetermined ratio, the accuracy of the image recognition model is regarded as being higher than the accuracy threshold.

15. The medical image recognition device of claim 12, wherein a plurality of predicted medical image piles is obtain by the image recognition model is based on the initial medical image piles formed based on the initial medical image slices.

16. The medical image recognition device of claim 15, wherein the processor is further configured to perform the following calculation:
subtracting a first target range corresponding to a first predicted medical image slice in the predicted medical image piles from a second target range corresponding to a second predicted medical image slice in the predicted medical image piles, so as to obtain an area difference; and
dividing the area difference by the first target range corresponding to the first predicted medical image slice to obtain one of the image change rates.

17. The medical image recognition device of claim 15, wherein the processor is further configured to perform the following calculation:
when the area of the target range corresponding to each of a plurality of predicted medical image slices in each predicted medical image pile increases gradually with time, the predicted medical image slices with positive image change rates are selected as the at least one training medical image slice; and,
when the area of the target range corresponding to each of the plurality of predicted medical image slices in each predicted medical image pile decreases gradually with time, the predicted medical image slices with negative image change rates are selected as the at least one training medical image slice.

18. The medical image recognition device of claim 15, wherein the processor is further configured to perform the following calculation:
selecting the initial medical image piles or the initial medical image slices corresponding to the predicted medical image pile or a plurality of predicted medical image slices with the image change rate greater than a change rate threshold as the at least one training medical image slice.

19. The medical image recognition device of claim 15, wherein the processor is further configured to perform the following calculation:
subtracting a first target volume corresponding to a first predicted medical image pile in the predicted medical image piles from a second target volume corresponding to a second predicted medical image pile in the predicted medical image piles, so as to obtain the volume difference; and dividing the volume difference by the second target volume to obtain one of the volume change rates.

20. The medical image recognition device of claim 12, wherein the processor is further configured to perform the following calculation:

inputting the initial medical image slices corresponding to the labeled medical image slices into the image recognition model to mark a prediction range corresponding to each of the initial medical image slices;

calculating an overlapping volume of each of the target ranges corresponding to the labeled medical image slices and the prediction range corresponding to each of the initial medical image slices; and dividing the overlapping volume by the target ranges corresponding to the labeled medical image slices to obtain a plurality of dice coefficients;

wherein in response to the dice coefficients are all within a range of predetermined values, or the number of dice coefficients above the accuracy threshold exceeds a predetermined ratio, the accuracy of the image recognition model is regarded as being higher than the accuracy threshold.

* * * * *